(12) United States Patent
Watanabe et al.

(10) Patent No.: US 10,073,064 B2
(45) Date of Patent: Sep. 11, 2018

(54) DEVICE HAVING ELEMENT ELECTRODE CONNECTED TO PENETRATING WIRE, AND METHOD FOR MANUFACTURING THE SAME

(71) Applicant: CANON KABUSHIKI KAISHA, Tokyo (JP)

(72) Inventors: Shinichiro Watanabe, Kawasaki (JP); Shinan Wang, Komae (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 530 days.

(21) Appl. No.: 14/640,287

(22) Filed: Mar. 6, 2015

(65) Prior Publication Data

US 2015/0263647 A1 Sep. 17, 2015

(30) Foreign Application Priority Data

Mar. 15, 2014 (JP) .................. 2014-052845

(51) Int. Cl.
*B81C 1/00* (2006.01)
*G01N 29/24* (2006.01)

(52) U.S. Cl.
CPC ..... *G01N 29/2406* (2013.01); *B81C 1/00095* (2013.01); *G01N 29/2418* (2013.01); *B81C 2201/0195* (2013.01); *G01N 2291/028* (2013.01); *G01N 2291/101* (2013.01)

(58) Field of Classification Search
CPC ....... G01N 2291/028; G01N 2291/101; G01N 29/2418; G01N 29/2406; B81C 2201/0195; B81C 1/00095; B81C 2201/0191; B81C 2201/0104; B81C 2201/0188; H02N 1/006; H02N 1/08
See application file for complete search history.

(56) References Cited

U.S. PATENT DOCUMENTS

| 7,022,609 | B2 * | 4/2006 | Yamamoto | ........ H01L 21/76898 216/13 |
| 7,232,754 | B2 * | 6/2007 | Kirby | ................ H01L 21/76898 257/E21.597 |
| 7,498,259 | B2 | 3/2009 | Yamano et al. | |
| 7,622,377 | B2 * | 11/2009 | Lee | ........................ H01L 21/486 257/E21.505 |

(Continued)

FOREIGN PATENT DOCUMENTS

| JP | 2006-13330 A | 1/2006 |
| JP | 2010-272956 A | 12/2010 |

*Primary Examiner* — Robert R Raevis
(74) *Attorney, Agent, or Firm* — Fitzpatrick, Cella, Harper & Scinto

(57) ABSTRACT

According to a method for manufacturing a device in which an electrode of an element is electrically connected to a penetrating wire in a substrate, a structure is prepared in which the element is arranged on the first substrate having a through hole formed therein: and a second substrate is prepared which has an electroconductive seed layer formed thereon. Then, a wall part is formed on the first substrate; a seed layer is joined to a face on an element side of the structure through a bonding layer; the bonding layer is removed; and the seed layer is exposed in the inside of the opening. The inside of the wall part and the through hole is filled with a conductor, with the use of the seed layer through electrolytic plating.

14 Claims, 6 Drawing Sheets

(56) References Cited

U.S. PATENT DOCUMENTS

| | | | |
|---|---|---|---|
| 7,629,249 B2* | 12/2009 | Borthakur | H01L 21/76846 257/E21.584 |
| 7,683,458 B2* | 3/2010 | Akram | H01L 21/6835 257/621 |
| 7,749,899 B2* | 7/2010 | Clark | H01L 21/76898 257/E21.585 |
| 7,902,643 B2* | 3/2011 | Tuttle | H01L 21/76898 257/659 |
| 7,915,736 B2* | 3/2011 | Kirby | H01L 21/76868 257/774 |
| 8,084,866 B2* | 12/2011 | Hiatt | H01L 21/6835 257/774 |
| 8,205,967 B2* | 6/2012 | Uyama | B41J 2/14145 347/54 |
| 8,278,738 B2* | 10/2012 | Nakashima | H01L 21/304 257/621 |
| 8,426,235 B2 | 4/2013 | Chang | |
| 8,448,333 B2* | 5/2013 | Uyama | H05K 3/4038 29/832 |
| 8,487,445 B1* | 7/2013 | Do | H01L 21/768 257/773 |
| 8,552,548 B1* | 10/2013 | Do | H01L 23/481 257/698 |
| 8,816,477 B2* | 8/2014 | Son | H01L 23/481 257/621 |
| 9,653,420 B2* | 5/2017 | Hiatt | H01L 24/14 |
| 2004/0043615 A1* | 3/2004 | Yamamoto | H01L 21/76898 438/689 |
| 2004/0048465 A1* | 3/2004 | Ito | H01L 21/2885 438/678 |
| 2004/0082100 A1* | 4/2004 | Tsukahara | H01L 23/5389 438/106 |
| 2006/0001173 A1 | 1/2006 | Yamano et al. | |
| 2007/0079986 A1* | 4/2007 | Kikuchi | H01L 21/6835 174/260 |
| 2009/0262605 A1* | 10/2009 | Wakabayashi | B06B 1/0292 367/181 |
| 2013/0015585 A1* | 1/2013 | Kosenko | H01L 23/481 257/774 |
| 2013/0032936 A1* | 2/2013 | Formosa | H04R 19/005 257/704 |

* cited by examiner

DEVICE HAVING ELEMENT ELECTRODE CONNECTED TO PENETRATING WIRE, AND METHOD FOR MANUFACTURING THE SAME

BACKGROUND OF THE INVENTION

Field of the Invention

The present invention relates to a device in which an electrode of an element such as a capacitance-type transducer that is used in an ultrasonic conversion element and the like is electrically connected to a penetrating wire, and a method for manufacturing the same.

Description of the Related Art

In recent years, various elements (sensor and the like) have been manufactured by a micromachining technology. Many of these sensors are produced with the use of a semiconductor process. As for these elements, not only the element itself is required to be miniaturized but also the device including a mounting portion is required to be miniaturized. Until now, an electrode for being connected to a circuit board or a wiring board has been arranged in the periphery of an element in many cases, and an area including the mounting portion has become large. As for one method for solving such a problem, there is a method of forming a penetrating wire on a substrate, and electrically connecting a wire of an element on the surface of the substrate to a wire on the rear face of the substrate. Thereby, the electrode can be formed on the rear face of the substrate, and a device which is provided with the element and includes the mounting portion can be miniaturized.

As for the above described technology, Japanese Patent Application Laid-Open No. 2006-13330 discloses a method for producing a penetrating wire substrate in the case where a functional element such as a cantilever is formed on the penetrating wire substrate. In this production method, a substrate having a through hole formed therein is bonded to a support, through a bonding layer (film resist) which has been formed on the surface of a plated seed layer on the above described support. After the bonding layer in a region which is linked to the through hole has been removed, a columnar electrode of copper is formed in the through hole. Finally, the support provided with the seed layer and the bonding layer are separated from the penetrating wire substrate. In addition, Japanese Patent Application Laid-Open No. 2010-272956 discloses a manufacturing method in the case where a capacitance type ultrasonic transducer has been formed on a penetrating wire substrate as a functional element. In this manufacturing method, the through hole is formed on a silicon substrate, polycrystalline silicon which becomes a wiring material is formed in the inside of the through hole, and then a capacitance type element is formed.

However, in the production method of Japanese Patent Application Laid-Open No. 2006-13330, when the bonding layer (film resist) in the region which is linked to the through hole is removed, a residue of the bonding layer must not be formed in order that the plated seed layer is exposed. In addition, it is not easy to confirm that the bonding layer has been removed, because the bonding layer is formed in the inside of the through hole, and the bonding layer needs to be over etched when the bonding layer is removed. However, when an over etching period of time becomes long, it becomes difficult to control a quantity of the spread in a lateral direction of a portion to be removed. As a result, the electrode material needs to have many margins of the quantity of spreading in the lateral direction of itself, and there is the case where the element and the penetrating electrode portion cannot be arranged at high density. In addition, in the manufacturing method of Japanese Patent Application Laid-Open No. 2010-272956, when the penetrating wire is formed of the polycrystalline silicon, it is not easy to lower the resistance of the penetrating wire because the polycrystalline silicon has high resistivity. Even when copper has been used for the wiring material, the number of steps for polishing both faces of the substrate increases, and the cost occasionally results in increasing.

SUMMARY OF THE INVENTION

With respect to the above described problems, a method of the present invention for manufacturing a device in which an electrode of an element is electrically connected to a penetrating wire in a substrate includes the following steps of: preparing a structure in which an element is arranged on a first substrate having a through hole formed therein; preparing a second substrate on which an electroconductive seed layer is formed; forming a wall part on the first substrate so that an opening which is linked to the through hole is formed; joining the seed layer to a face on the element side of the structure through a bonding layer; removing the bonding layer which has entered the inside of the through hole and the wall portion to expose the seed layer in the inside of the opening; and filling the inside of the wall part and the through hole with a conductor, by using the seed layer through electrolytic plating.

With respect to the above described problems, a device of the present invention, in which an electrode of an element is electrically connected to a penetrating wire in a through hole in a substrate, includes: a wall part which has an opening that is linked to the through hole formed on a face of the substrate, on which the element is arranged; and a conductor which is filled in the inside of the opening of the wall part and the through hole, and forms the penetrating wire.

In addition, the present invention includes the following method for manufacturing the device.

Specifically, a method for manufacturing a device in which an electrode of an element is electrically connected to a wire that reaches a second face side of a substrate on which the element is provided, from a first face side of the substrate, includes the steps of: preparing a first substrate on which a hole part, that reaches the second face side of the substrate from the first face side thereof, and the element are formed; preparing a second substrate on which an electroconductive seed layer is formed; forming a wall part on the first substrate so that an opening is formed which is linked to the hole part; laminating the seed layer with a face of the first substrate, on the side on which the wall part is formed, through a bonding layer; removing the bonding layer which is positioned in the inside of the wall part of the laminated substrate to expose the seed layer in the inside of the opening; and filling the inside of the wall part and the hole part with a conductor, by using the seed layer through electrolytic plating.

Furthermore, the present invention also includes the following method for manufacturing the device.

Specifically, a method for manufacturing a device in which an electrode of an element is electrically connected to a wire that reaches a second face side of a substrate on which the element is provided, from a first face side of the substrate, includes the steps of: preparing a first substrate on which a hole part, that reaches the second face side of the substrate from the first face side thereof, and the element are formed; preparing a second substrate on which an electroconductive seed layer is formed; laminating the seed layer with the side face of the first substrate on which the element is formed; and filling the inside of the hole part with a conductor, by using the seed layer through electrolytic plating.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

In a method of the present invention for manufacturing a device in which an electrode of an element is electrically connected to a penetrating wire in a substrate, a structure is prepared in which an element is arranged on a first substrate having a through hole therein: and a second substrate is prepared which has an electroconductive seed layer thereon. Then, a wall part such as an annular projecting portion is formed on the first substrate so that an opening is formed which is linked to the through hole; a seed layer is joined to a face on an element side of the structure through an bonding layer; the bonding layer is removed which has entered the inside of the through hole and the wall part; and the seed layer is exposed in the inside of the opening. The inside of the wall part and the through hole is filled with a conductor, with the use of this exposed seed layer through electrolytic plating. Due to the wall part having the opening therein which is linked to the through hole, it can be suppressed that the conductor spreads to the outside of the through hole on the face on the element side of the structure; and the element and the penetrating wire portion can be arranged even at high density.

Figure 1A:
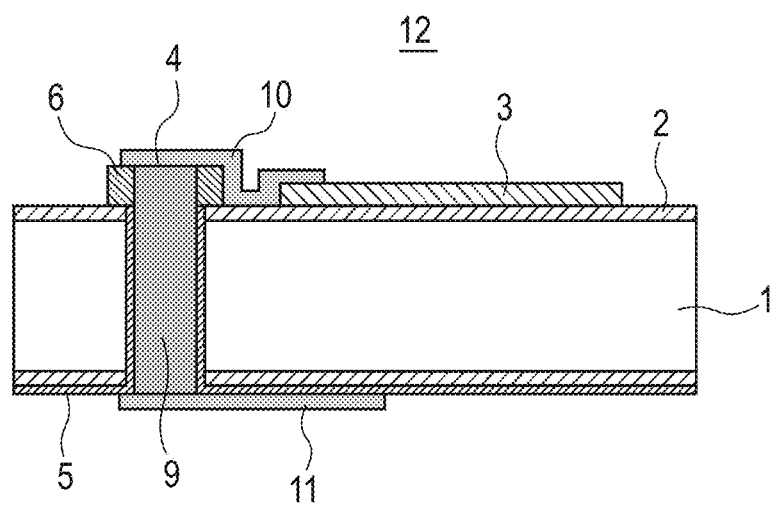
FIGS. 1A and 1B are a view for describing an example of a device of the present invention, in which an element is connected to a penetrating wire in a substrate.
Figure 1B:
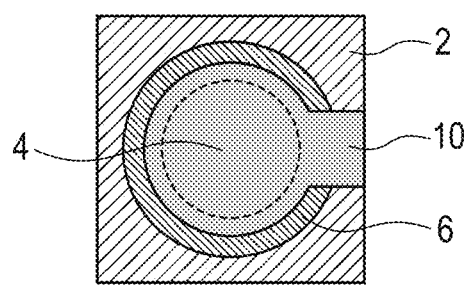

A device provided with an electromechanical conversion unit, to which a method for producing the device according to one embodiment of the present invention is applied, in which an element is connected to a penetrating wire in a through hole of a substrate, is illustrated in FIG. 1 A and FIG. 1B. FIG. 1A illustrates a sectional view of the device provided with an electromechanical conversion unit such as a capacitance-type transducer, which is an element; and FIG. 1B illustrates a top plan view of the device in the vicinity of a through hole 4. The electromechanical conversion unit is, for instance, a capacitance-type transducer or the like, which has a cell having a structure in which a vibrating membrane is vibratably supported that includes a second electrode which is provided so as to face a first electrode and sandwich a gap between itself and the first electrode. A device 12 provided with the electromechanical conversion unit has a functional element 3 formed on an insulating layer 2 on an active face (face on which element is arranged) of a substrate 1. The substrate 1 can employ, for instance, a silicon wafer and glass. When the substrate 1 is a glass substrate, the insulating layer 2 does not need to be formed. An insulating material such as a silicon oxide film and a silicon nitride film can be used for the insulating layer 2. A transistor and the like can also be provided as the functional element 3, in addition to various electromechanically convertable elements. An upper wire 10 which is connected to the functional element 3 is electrically connected to a conductor 9 in the inside of the through hole 4 which is in the state of being insulated from the substrate 1 by an insulating film 5, and is further electrically connected to a lower wire 11 on the rear face in an opposite side to the active face of the substrate 1. The conductor 9 which functions as the penetrating wire can be formed with the use of an electrolytic plating method, but a material which contains copper as a main material is desirably employed in consideration of the cost and the lowering of the resistance. The upper wire 10 and the lower wire 11 may be formed of a metal or an alloy, and are desirably a material having low resistance, which contains aluminum as a main material. A silicon oxide film, a silicon nitride film and the like can be used as the insulating film 5 for the inner wall face of the through hole and the rear face of the substrate.

Furthermore, the wall part 6 which is an annular projecting portion or the like is formed so that the inner circumference comes in contact with the outer circumferential line of the through hole 4, or the inner circumference includes the outer circumferential line of the through hole 4, on the active face of the substrate 1. Specifically, the wall part is formed in the vicinity of the outer circumference of the through hole so as to surround the through hole. The wall part 6 is necessary when the conductor 9 is formed in the through hole 4, and may be removed in a step after the step of having formed the conductor 9. In the above configuration, the state in which the wall part 6 is formed so that the inner circumference comes in contact with or includes the outer circumferential line of the through hole 4 shall be described as a state in which the wall part 6 is formed so that the opening is linked to the through hole 4. As for the wall part 6, an insulating film of a dry film resist, a resist, polyimide or the like can be used. Due to this configuration, it can be suppressed that the conductor 9 spreads in a lateral direction on the active face of the substrate 1, by the wall part 6 having the opening which is linked to the through hole 4, and the device can be produced in which the element and the penetrating wire portion can be arranged at high density. In FIG. 1A, one penetrating wire is arranged for one functional element 3, but a plurality of penetrating wires may be arranged for one functional element, and one penetrating wire or a plurality of penetrating wires may be formed for a plurality of functional elements.

Figure 2A:
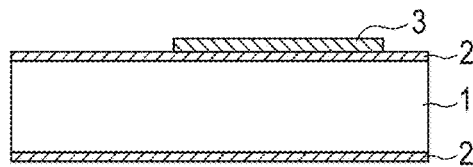
FIGS. 2A, 2B, 2C, 2D, 2E, 2F, 2G, 2H, 2I, 2J, 2K and 2L are a sectional view for describing an example of a method for manufacturing the device of the present invention.

An example of a method for producing the device according to the present invention will be described below with reference to FIG. 2A to FIG. 2G and FIG. 2H to FIG. 2L. In FIG. 2A, the first substrate 1 is prepared, and the insulating layer 2 is further formed on the upper and lower faces of the substrate 1. A silicon wafer or glass, for instance, can be used as the substrate 1. When the substrate 1 is a glass substrate, the insulating layer 2 may not be formed. The thickness of the substrate 1 is, for instance, 100 to 1,000 μm. When the substrate 1 is the silicon wafer, the silicon wafer may be formed of any one of high-resistivity silicon and low-resistivity silicon. Here, the production method will be described below by taking the case as an example, where the substrate 1 is formed of the low-resistance silicon having a resistivity of 0.1 Ωcm or less. An insulating material such as a silicon oxide film and a silicon nitride film is formed as the insulating layer 2. The insulating layer 2 can be formed of a single layer film or a multilayer film. Here, a silicon oxide film having a thickness of 0.1 to 1 μm is formed by thermal oxidation, for instance, as the insulating layer 2. Next, the functional element 3 is formed on the insulating layer 2 on the active face of the substrate 1. An element which is provided with various types of electromechanically convertable elements or other elements can be formed as the functional element 3.

Figure 2B:
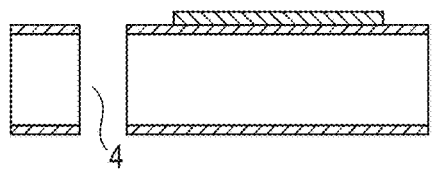
Figure 2C:
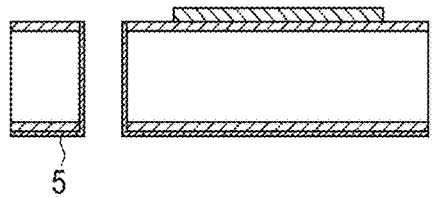

Furthermore, as is illustrated in FIG. 2B, the through hole 4 is formed with the use of a deep-reactive ion etching (D-RIE: Deep-Reactive Ion Etching) technology for silicon. When a transverse sectional shape of the through hole 4 is a circle, for instance, the diameter is 10 to 100 μm. The through hole may be a circle, a polygon or the like, and the longitudinal sectional shape may be vertical or may also be tapered. In addition, the inner wall face of the through hole 4 may be smoothened, as needed. Furthermore, as is illustrated in FIG. 2C, the insulating film 5 is formed on the inner wall of the through hole 4. The insulating film 5 is desirably formed from a material having high insulating properties such as a silicon oxide film, a silicon nitride film, aluminum oxide and tantalum pentoxide, for instance, and is desirably formed at a temperature lower than a temperature at which the functional element 3 is formed. The thickness of the insulating layer 5 can be determined according to a performance of an electromechanical conversion element or the like. The thickness of the insulating film 5 is, for instance, 0.1 to 4 μm. In the case where the silicon oxide film is formed, there are methods such as chemical vapor deposition (CVD: Chemical Vapor Deposition) and atomic layer deposition (ALD: Atomic Layer Deposition). The insulating film 5 may be a single layer film or a multilayer film, and a barrier layer for preventing the bonding layer and the conductor 9 from diffusing into a gap between the inner wall of the through hole 4 and the insulating film 5 may also be formed, as needed. In the present embodiment, the insulating film 5 is formed also on the rear face of the substrate 1.

Figure 2D:
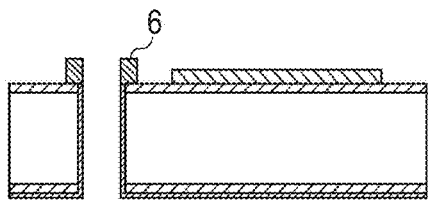

Next, as is illustrated in FIG. 2D, the wall part 6 is formed so that the opening is linked to the through hole 4. The wall part 6 may employ a dry film resist, a photoresist, a resin such as polyimide, an insulating material, a metal material and the like; but desirably employs a material having insulating properties. The wall part 6 is formed, for instance, by affixing a negative type dry film resist onto an active face of the substrate 1 by a laminating method or a roller pressure-bonding method; and then submitting the resist to light exposure, development and curing. The film thickness of the dry film resist is, for instance, 5 to 20 μm, but is acceptable as long as the film thickness is thicker than the height of the functional element 3. The wall part 6 is formed in the step of FIG. 2D, but may be formed prior to the step of forming the through hole 4 of FIG. 2B, or also prior to the step of forming the insulating film 5 of FIG. 2C. The thickness in the lateral direction of the wall part 6 may be a thickness which is not separated when a conductor is formed. The functional element 3 also may be formed after the step of forming the through hole 4 of FIG. 2B, after the step of forming the insulating film 5 of FIG. 2C, or also after the step of forming the wall part 6 of FIG. 2D. At this time, an appropriate portion may be masked.

Figure 2E:

Furthermore, as is illustrated in FIG. 2E, a support 7 is prepared that is a second substrate having electroconductivity at least on the surface (specifically, second substrate having electroconductive seed layer formed thereon). The support 7 can employ a metal, an insulating material or the like, but when the support 7 has employed the insulating material, a metal film needs to be formed on the surface of the insulating material as the seed layer. For instance, stainless steel, nickel, titanium or the like can be used as a material of the support 7, but it is desirable to select a material having resistance to a plating solution in a step of forming the conductor 9 after this.

Figure 2F:
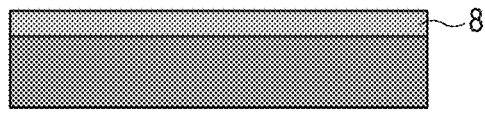

Furthermore, as is illustrated in FIG. 2F, a bonding layer 8 is formed on a face having electroconductivity (seed layer) on the support 7. A non-ionic surfactant can be used as the bonding layer 8, and polyoxyethylene lauryl ether, polyvinyl alcohol and the like can be employed, for instance. The bonding layer 8 can be formed with a dipping method, a spin coating method, a spray coating method or the like. The thickness of the bonding layer is, for instance, 4 to 20 μm, and may be such a thickness by which a sufficient adhesion strength is obtained.

Figure 2G:
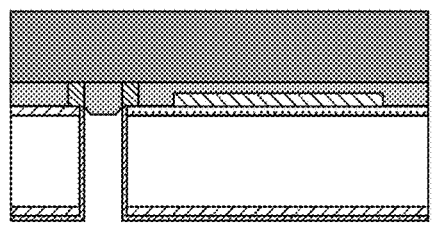

Furthermore, as is illustrated in FIG. 2G, a face (seed layer) having electroconductivity on the support 7 is joined to the wall part 6 of the substrate 1 and the active face of the substrate 1, while a load is applied to the faces at a temperature of a melting point of the bonding layer 8 or higher. The faces can be laminated to each other on a hot plate or in an oven, for instance, in such a state that a load is applied to the faces. By this operation, the face having electroconductivity on the support 7 and the wall part 6 can be laminated to each other so that a gap is not formed therebetween. The bonding layer may be formed on the active face of the substrate 1.

Figure 2H:
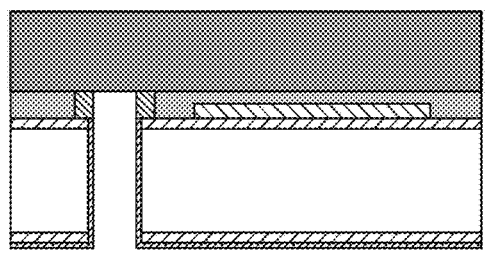

Next, as is illustrated in FIG. 2H, the bonding layer 8 in the inside of the through hole 4 and the wall part 6 is removed, and the face (seed layer) having electroconductivity on the support 7 is exposed. As for a method of removing the bonding layer 8, there is a method of infiltrating a solvent being capable of dissolving the non-ionic surfactant therein into the through hole 4, and making the solvent dissolve the bonding layer. Water, isopropyl alcohol, acetone, methanol, ethanol and the like can be used as the solvent being capable of dissolving the non-ionic surfactant therein, but the bonding layer 8 can be removed also by dry etching with the use of oxygen plasma, and the like. Any method is acceptable as long as the method can dissolve the bonding layer 8, and the method is not limited to the solvent. The wall part 6 is linked to the through hole 4, and accordingly when the bonding layer 8 is removed, the region from which the bonding layer is removed can be limited to only the inside of the through hole 4 and the wall part 6.

Figure 2I:
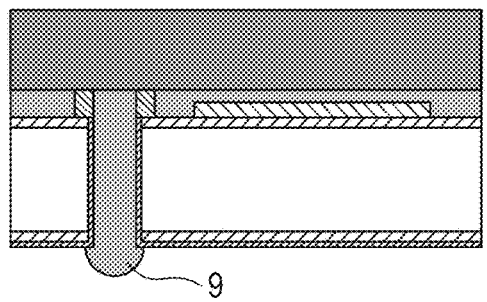

Furthermore, as is illustrated in FIG. 2I, the conductor 9 is filled in the inside of the through hole 4 from the face of the seed layer having electroconductivity on the support 7 in the inside of the through hole 4 and the wall part 6, by electrolytic plating. Usable materials for the conductor 9 include, for instance, copper, nickel, and a material which contains an alloy thereof as a main material. Because the wall part 6 is linked to the through hole 4, a solvent being capable of dissolving a non-ionic surfactant therein contained in a plating solution does not remove the bonding layer 8, and a penetrating wire region in which the conductor 9 is filled can be controlled to be only the inside of the through hole 4. Thereby, it can be suppressed that the conductor 9 spreads in a lateral direction to the outside of the outer circumference of the through hole 4 on the active face of the substrate 1, and the element and the penetrating wire portion can be arranged at high density.

Figure 2J:
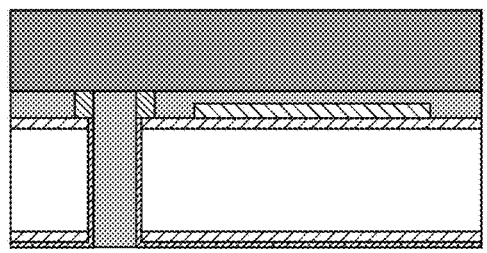
Figure 2K:
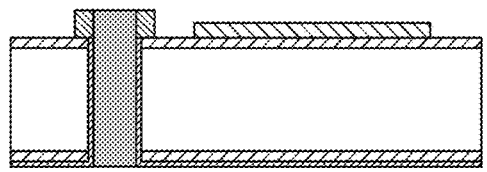

Next, as is illustrated in FIG. 2J, a portion which projects from the through hole 4 on the rear face of the substrate 1 is flattened by chemical mechanical polishing (CMP: Chemical Mechanical Polish). Furthermore, as is illustrated in FIG. 2K, the support 7 and the bonding layer 8 are separated from the substrate 1. By being heated to a temperature of the melting point of the non-ionic surfactant or higher, the non-ionic surfactant is converted from a solid to a liquid. By this operation, flexibility is given to the non-ionic surfactant. Then, the adhesion force of the bonding layer 8 is lowered, and the bonding layer can be easily separated.

Figure 2L:
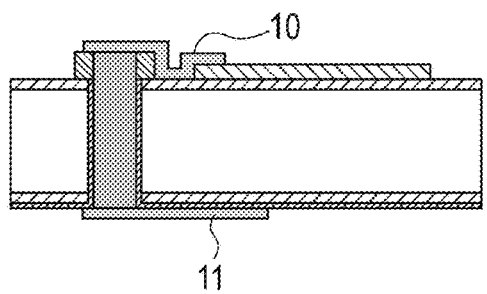

Furthermore, as is illustrated in FIG. 2L, the upper wire 10 and the lower wire 11 are formed on the active face of the substrate 1 and the rear face in an opposite side to the active face, respectively, and are electrically connected to the conductor 9 of the penetrating wire. The upper wire 10 and the lower wire 11 may be formed from metal or alloy, and is desirably formed from a low-resistance metal which contains copper or aluminum as a main material. The film thicknesses of the upper wire 10 and the lower wire 11 are each 0.1 to 1 µm, for instance. A sputtering method, a vapor-deposition method or the like can be used as a method of forming the wire.

The present invention will be described below with reference to specific Examples.

EXAMPLE 1 (When Capacitance Type Ultrasonic Transducer is Formed)

Figure 3A:
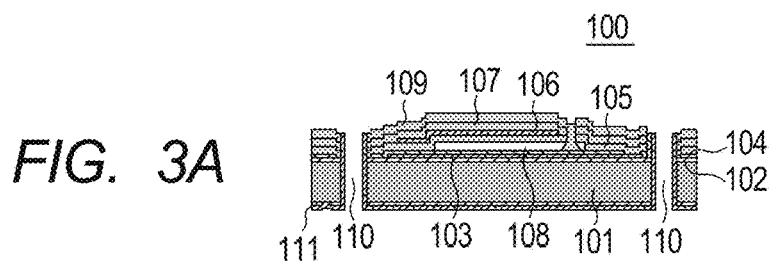
FIGS. 3A, 3B. 3C, 3D, 3E, 3F, 3G, 3H, 3I, 3J and 3K are a sectional view for describing Example 1 of the method for manufacturing the device of the present invention.

A method for producing a device having a capacitance type ultrasonic transducer formed on a penetrating wire substrate will be described below with reference to FIG. 3A to FIG. 3H and FIG. 3I to FIG. 3K, as Example 1 using the present invention. The ultrasonic transducer of the device 100 has such a cell structure that two parallel flat-plate electrodes are arranged so as to face each other while having a gap (cavity) therebetween, for instance, and can transmit and receive ultrasonic waves by the vibration of one vibratable electrode plate. The configuration of the ultrasonic transducer will be described below with reference to the sectional view of FIG. 3A. The ultrasonic transducer has a vibrating film that includes a second electrode 106 which is formed so as to have an approximately vacuum gap 108 between the second electrode 106 and the first electrode 103, provided on a silicon substrate 101 which is a first substrate. The vibrating film is provided with the second electrode 106, a first membrane 105, a second membrane 107 and a third membrane 109, and is vibratably supported. In FIG. 3A, the vibrating film has a configuration of having four layers, but can also adopt a three-layer configuration or other configurations. Furthermore, as an example of wiring for driving, the first electrode 103 is set at a bias electrode, and the second electrode 106 is set at a signal extracting electrode.

In the production method, a first insulating layer 102 for insulating the substrate is formed on the silicon substrate 101. The silicon substrate 101 has a thickness of 300 µm, is desirably a low-resistivity silicon substrate, and can have a resistivity of 0.1 Ωcm or less. The insulating layer 102 is a silicon oxide film which has been formed by thermal oxidation and has a thickness of 1 µm. Furthermore, a first electrode 103 is formed on the insulating layer 102. The first electrode 103 is formed from titanium or tungsten by a sputtering method, and has a thickness of 0.05 µm. An insulating layer 104 may also be formed on the first electrode 103.

Furthermore, a first membrane 105, a second membrane 107 and a third membrane 109 are silicon nitride films which have been formed by Plasma Enhanced-Chemical Vapor Deposition (PE-CVD). The membranes are each formed so as to have a tensile stress of approximately 150 MPa or less. The thicknesses of the first to third membranes are 0.4 µm, 0.3 µm and 0.7 µm, respectively. The gap 108 has a diameter of 31 µm and a height of 0.2 µm. The second electrode 106 is formed from titanium, aluminum or an alloy containing aluminum by a sputtering method, and has a diameter of 27 µm and a thickness of 0.1 µm.

In FIG. 3A, after the capacitance type ultrasonic transducer has been formed, a through hole 110 is formed. The through hole 110 is formed with the use of a deep-reactive ion etching (D-RIE) technology for silicon. A transverse sectional shape of the through hole 110 is an approximate circle, and the diameter of the circle is 50 µm. Furthermore, an insulating film 111 is formed on the inner wall face of the through hole 110 and the rear face of the silicon substrate 101. As for the insulating film 111, a silicon oxide film is formed so that the thickness of the inner wall of the through hole 110 becomes 1 µm. In this case, the silicon oxide film is formed with the use of TEOS-CVD (Chemical Vapor Deposition) so that the film can be formed at a film-forming temperature of the above described membrane or lower.

Figure 3B:
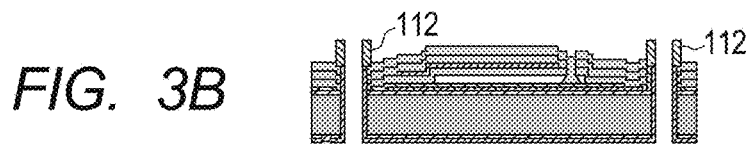
Figure 3C:
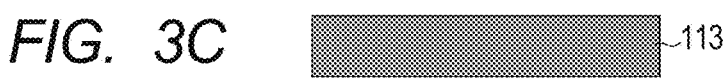
Figure 3D:

Furthermore, as is illustrated in FIG. 3B, a wall part 112 is formed so as to be linked to the through hole 110. The wall part 112 is formed by an operation of affixing a negative type of dry film resist onto the active face of the substrate 101 with a laminating method, and then submitting the resist to light exposure, development and curing. The film thickness of the dry film resist is 5 µm, but may be larger than the height of the capacitance type ultrasonic transducer. Furthermore, as is illustrated in FIG. 3C, a support 113 is prepared which is a second substrate having an electroconductive seed layer thereon. A stainless plate having a thickness of 300 µm was used as the support 113. Furthermore, as is illustrated in FIG. 3D, a bonding layer 114 of a non-ionic surfactant is formed on any one of the surfaces of the support 113. Polyoxyethylene lauryl ether was used for the bonding layer 114 of the non-ionic surfactant. The support 113 is spin-coated with a mixed solvent of cyclopentanone and acetone, which has dissolved polyoxyethylene lauryl ether therein, and is left for 30 minutes to have a solid layer of polyoxyethylene lauryl ether formed thereon.

Figure 3E:
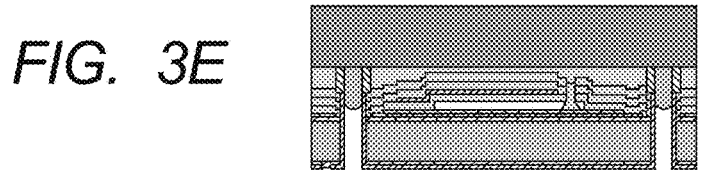
Figure 3F:
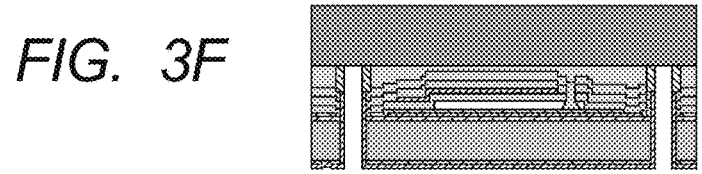

Next, as is illustrated in FIG. 3E, the support 113 and the wall part 112 are laminated with each other, while a load is applied thereto in a vacuum oven at 75° C. under a reduced pressure. By this operation, the support 113 and the wall part 112 can be strongly laminated with each other so as not to form a gap between the surface of the support 113 and the wall part 112. Thereby, an electroconductive layer which becomes a seed layer for plating can be formed. Furthermore, as is illustrated in FIG. 3F, a structure to which the support 113 is joined is immersed into water, and the bonding layer 114 in the inside of the through hole 110 and the wall part 112 is dissolved. At this time, a region from which the bonding layer 114 is removed is limited only to the inside of the through hole 110 and the wall part 112, because the wall part 112 is formed so as to be linked to the through hole 110.

Figure 3G:
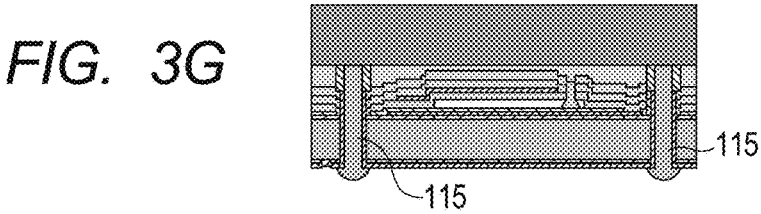
Figure 3H:
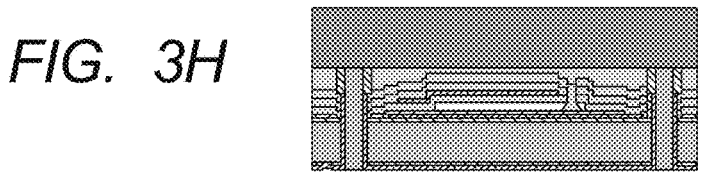

Furthermore, as is illustrated in FIG. 3G, copper 115 is filled in the inside of the through hole 110 from the electroconductive support 113 in the inside of the through hole 110 and the wall part 112, by a copper plating method which uses a plating solution of copper sulfate. Because the wall part 112 is formed so as to be linked to the through hole 110, a solvent being capable of dissolving the non-ionic surfactant contained in the plating solution does not dissolve the bonding layer 114 in the outside of the through hole 110, and a penetrating wire region in which a conductor 115 is filled can be controlled to be only the inside of the through hole 110. Thereby, it can be suppressed that the conductor 115 spreads in a lateral direction to the outside of the outer circumference of the through hole 110 on the active face of the substrate 101, on which the element is formed, and the element and the penetrating wire portion can be arranged at high density. Furthermore, as is illustrated in FIG. 3H, a portion which projects from the through hole 110 on the rear face of the substrate 101 after plating is flattened by chemical mechanical polishing (CMP).

Figure 3I:
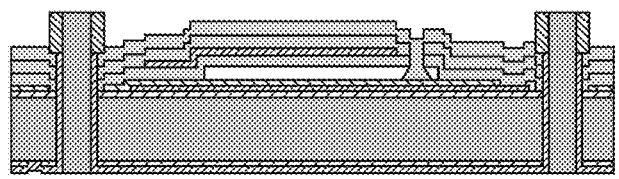
Figure 3J:
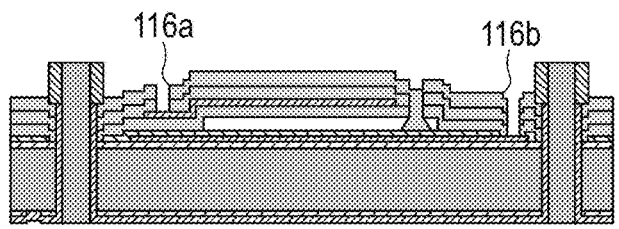

Next, as is illustrated in FIG. 3I, the support 113 and the bonding layer 114 are separated from the substrate 101. As for the separation method, the substrate after having been subjected to the chemical mechanical polishing was placed on a hot plate at 80° C., and the substrate was displaced by a force which has been applied to the substrate in a horizontal direction. By this operation, the substrate 101 and the support 113 can be easily separated from each other. Furthermore, as is illustrated in FIG. 3J, electrode holes 116a and 116b are formed for electrically connecting the conductor 115 to the second electrode 105, and electrically connecting the conductor 115 to the first electrode 103, respectively. The electrode holes 116a and 116b are formed with the use of a chemical dry etching apparatus.

Figure 3K:
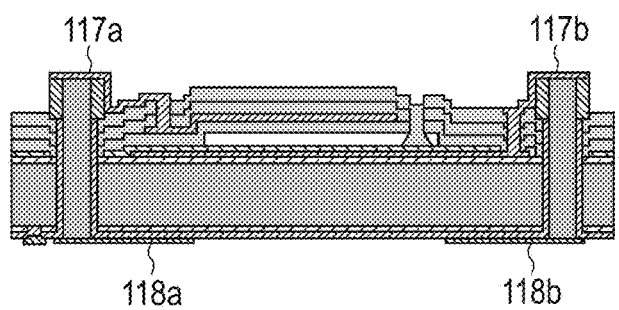

Furthermore, as is illustrated in FIG. 3K, upper wires 117a and 117b and lower wires 118a and 118b are formed on the active face and the rear face of the substrate 101, respectively, and are electrically connected to the conductor 115 of the penetrating wire. The upper wires 117a and 117b and the lower wires 118a and 118b are each formed from aluminum or an aluminum alloy by a sputtering method, and the film thicknesses of the wires are each 0.5 µm.

EXAMPLE 2 (When Wall Part is Removed)

Figure 4:
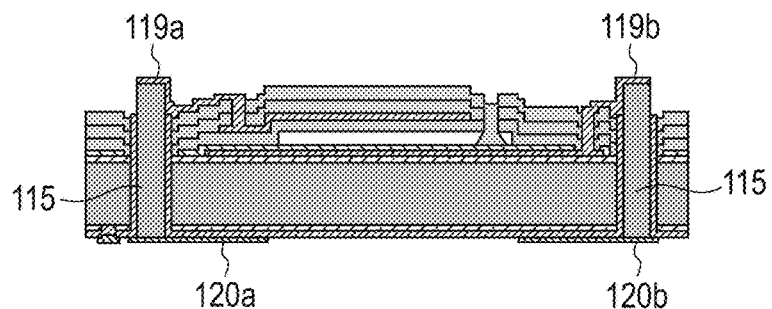
FIG. 4 is a sectional view for describing Example 2 of the method for manufacturing the device of the present invention.

The production method in Example 2 of the present invention will be described below with reference to FIG. 4. The manufacturing method in Example 2 is the same as the manufacturing method to the step of FIG. 3I in Example 1 of the present invention, but is different from that in Example 1 in a point that the wall part 112 is removed. A method of removing the wall part 112 by asking while using oxygen plasma is employed as a method for removing the wall part 112. FIG. 4 shows a configuration in the case where the wall part 112 has been removed. Upper wires 119a and 119b and lower wires 120a and 120b are formed on the active face and the rear face of the substrate 101, respectively, and are each electrically connected to the conductor 115 of a penetrating wire. When the wall part 112 is removed, there is such an effect that the reliability of a connected part is enhanced. Specifically, a region to be connected to the upper wires 119a and 119b can be increased also to another region in addition to the upper face of the conductor 115. For instance, the upper wire can be electrically connected to the side wall of the conductor 115 which projects from the active face of the substrate 101. By this operation, even when a region in which the conductor 115 projects from the substrate 101 has increased, stable electric connection is enabled. Other points are the same as those in Example 1.

EXAMPLE 3

Figure 5A:
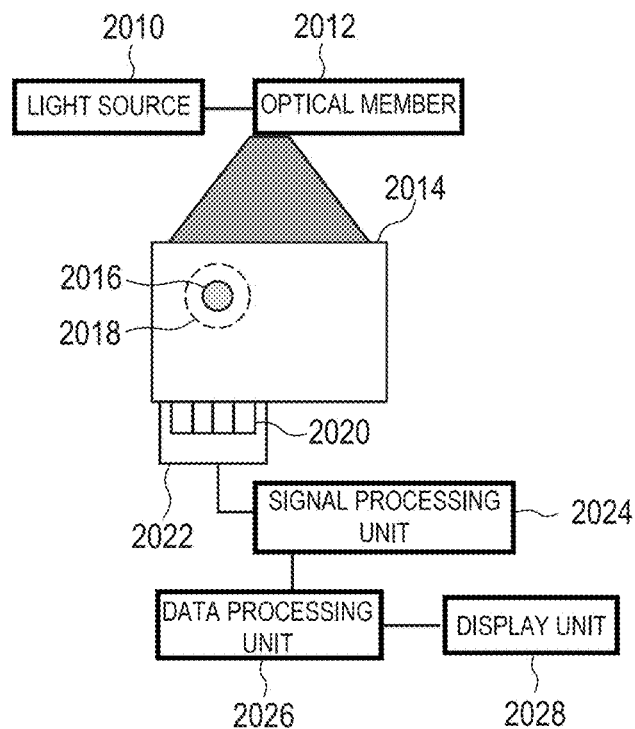
FIGS. 5A and 5B are a view illustrating an example of a subject information obtaining apparatus of the present invention.

FIG. 5A illustrates an example of a subject information obtaining apparatus which uses a photoacoustic effect. Pulsed light which has been oscillated from a light source 2010 irradiates a subject 2014 through an optical member 2012 such as a lens, a mirror and an optical fiber. A light absorber 2016 in the inside of the subject 2014 absorbs the energy of the pulsed light, and generates a photoacoustic wave 2018 which is an acoustic wave. A device 2020 which includes an electromechanical conversion unit of the present invention in a probe 2022 receives the photoacoustic wave 2018, converts the photoacoustic wave into an electrical signal, and outputs the electrical signal to a signal processing unit 2024. The signal processing unit 2024 performs signal processing such as A/D conversion and amplification, for the input electrical signal, and outputs the processed electrical signal to a data processing unit 2026. The data processing unit 2026 acquires subject information (characteristic information which reflects optical characteristic value such as optical absorption coefficient of subject) by using the input signal, as image data. Here, a unit which includes the signal processing unit 2024 and the data processing unit 2026 shall be referred to as a processing unit. A display unit 2028 displays an image based on image data which has been input from the data processing unit 2026. As has been described above, the subject information obtaining apparatus of the present example includes the device according to the present invention, the light source and the processing unit. The device receives a photoacoustic wave generated from the subject which has been irradiated with light that has been oscillated from the light source, and converts the photoacoustic wave into an electrical signal. The processing unit acquires information on the subject by using the electrical signal.

Figure 5B:
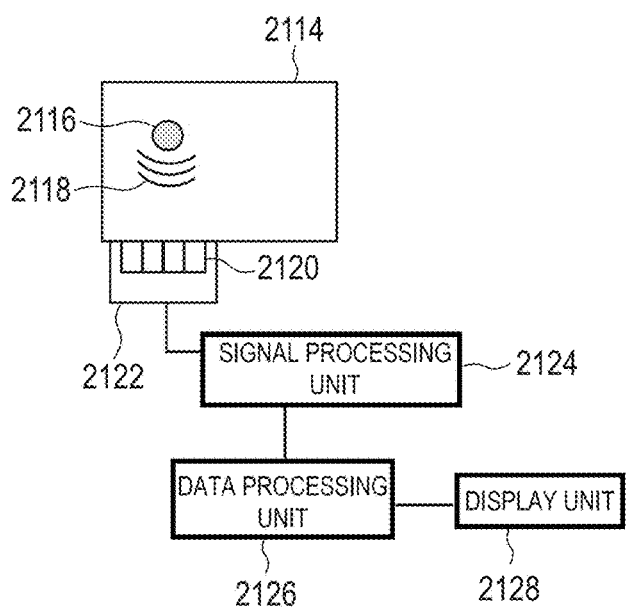

FIG. 5B illustrates the subject information obtaining apparatus such as an ultrasonic echo diagnostic apparatus which uses a reflection of an acoustic wave. An acoustic wave is transmitted from a device 2120 which contains the electromechanical conversion unit of the present invention in a probe 2122 to a subject 2114, and is reflected by a reflector 2116. The device 2120 receives a reflected acoustic wave (reflected wave) 2118, converts the acoustic wave into an electrical signal, and outputs the electrical signal to a signal processing unit 2124. The signal processing unit 2124 performs signal processing such as A/D conversion and amplification, for the input electrical signal, and outputs the processed electrical signal to a data processing unit 2126. The data processing unit 2126 acquires subject information (characteristic information which reflects difference of acoustic impedance) by using the input signal, as image data. Here as well, a unit which includes the signal processing unit 2124 and the data processing unit 2126 shall be referred to as a processing unit. A display unit 2128 displays an image based on image data which has been input from the data processing unit 2126. As has been described above, the subject information obtaining apparatus of the present example includes the device of the present invention, and the processing unit which acquires information on the subject by using the electrical signal that the device outputs. The device receives an acoustic wave transmitted from the subject, and outputs an electrical signal.

Incidentally, the probe may be a mechanically scanning probe, or may also be a probe (handheld type) which a user such as a doctor and an operator moves with respect to the subject. In addition, in the case of the apparatus which uses the reflected wave as is illustrated in FIG. 5B, the probe which transmits the acoustic wave may be provided separately from a probe that receives the acoustic wave. Furthermore, it is also acceptable to form an apparatus which has both functions of the apparatuses in FIG. 5A and FIG.

5B, and make the apparatus acquire both of the subject information which reflects the optical characteristic value of the subject, and the subject information which reflects a difference of an acoustic impedance. In this case, the device 2020 in FIG. 5A may be structured so as to not only receive a photoacoustic wave but also transmit the acoustic wave and receive the reflected wave.

According to the present invention, the wall part is formed so as to be linked to a through hole in a substrate on which an element is formed, and the second substrate and a face on the element side of the structure are joined to each other through a bonding layer. The bonding layer in the inside of the through hole and the opening is removed to expose a seed layer, and then the inside of the through hole is filled with a conductor. Due to the wall part, it can be suppressed that the conductor spreads in a lateral direction to the outside of the outer circumference of the through hole, on the face on the element side of the structure. Accordingly, the element and the penetrating wire portion can be arranged even at high density.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-052845, filed Mar. 15, 2014, which is hereby incorporated by reference herein in its entirety.

What is claimed is:

1. A method for manufacturing a device in which an electrode of an element, which is provided on or over a substrate, is electrically connected to a wire that reaches a second face side of the substrate from a first face side of the substrate, the method comprising the steps of:
   preparing a first substrate having a hole part, which reaches a second face side of the first substrate from a first face side thereof, and the element provided on or over the first substrate through an insulating layer;
   preparing a second substrate on which an electroconductive seed layer is formed;
   forming a wall part projecting from the insulating layer on the first substrate so that an opening is formed and is linked to the hole part;
   laminating the seed layer with the first substrate on a side thereof on which the wall part is formed, through a bonding layer to provide a laminated substrate;
   removing the bonding layer, which is positioned in an inside of the wall part of the laminated substrate, to expose the seed layer through the opening; and
   filling the inside of the wall part and the hole part with a conductor, by using the seed layer through electrolytic plating.

2. The method for manufacturing the device according to claim 1, further comprising a step of separating the second substrate from the laminated substrate.

3. The method for manufacturing the device according to claim 2, further comprising a step of removing the wall part after having separated the second substrate.

4. The method for manufacturing the device according to claim 1, wherein the hole part has an insulating film formed on an inner wall face of the hole part.

5. The method for manufacturing the device according to claim 1, wherein the wall part has insulating properties.

6. The method for manufacturing the device according to claim 1, wherein the conductor is a metal.

7. The method for manufacturing the device according to claim 1, wherein the wall part is formed in a vicinity of an outer circumference of the hole part so as to surround the hole part.

8. The method for manufacturing the device according to claim 1, wherein the element is a capacitance-type transducer.

9. The method for manufacturing the device according to claim 1, further comprising a step of chemomechanically polishing a face opposite to a face on an element side of the laminated substrate, after the step of filling the inside of the wall part and the hole part with the conductor.

10. The method for manufacturing the device according to claim 1, wherein the wall part is formed on a face on an element side of the laminated substrate.

11. The method for manufacturing the device according to claim 1, further comprising a step of forming the bonding layer on the seed layer of the second substrate.

12. The method for manufacturing the device according to claim 1, wherein the wall part is formed to be higher than the element.

13. The method for manufacturing the device according to claim 1, wherein a material of the wall part is different from that of the insulating layer.

14. The method for manufacturing the device according to claim 13, wherein the material of the wall part includes a resin.

* * * * *